US009623004B2

(12) United States Patent
Kaytor et al.

(10) Patent No.: US 9,623,004 B2
(45) Date of Patent: Apr. 18, 2017

(54) ADMINISTRATION OF A THERAPEUTIC AMOUNT OF GENISTEIN TO MITIGATE ERECTILE DYSFUNCTION RESULTING FROM RADIATION THERAPY FOR PROSTATE CANCER ONLY THROUGHOUT A DEFINED ADMINISTRATION PERIOD COMMENCING SHORTLY BEFORE AND CONCLUDING AFTER RADIATION THERAPY

(71) Applicant: Humanetics Corporation, Minneapolis, MN (US)

(72) Inventors: Michael D. Kaytor, Maplewood, MN (US); John L. Zenk, Eden Prairie, MN (US); Geoffrey E. Schroeder, Woodbury, MN (US); Zeljko Vujaskovic, Baltimore, MD (US); Isabel Lauren Jackson, Baltimore, MD (US)

(*) Notice: Subject to any disclaimer, the term of this patent is extended or adjusted under 35 U.S.C. 154(b) by 0 days.

(21) Appl. No.: 14/446,906

(22) Filed: Jul. 30, 2014

(65) Prior Publication Data
US 2015/0038572 A1 Feb. 5, 2015

Related U.S. Application Data

(60) Provisional application No. 61/861,642, filed on Aug. 2, 2013.

(51) Int. Cl.
| *A61K 31/35* | (2006.01) |
| *A61K 31/353* | (2006.01) |
| *A61K 9/00* | (2006.01) |
| *A61K 31/352* | (2006.01) |

(52) U.S. Cl.
CPC ............ *A61K 31/353* (2013.01); *A61K 9/006* (2013.01); *A61K 31/352* (2013.01)

(58) Field of Classification Search
CPC ..... A61K 31/353; A61K 9/006; A61K 31/352
USPC ......................................................... 514/456
See application file for complete search history.

(56) References Cited

U.S. PATENT DOCUMENTS

| 5,523,087 A | 6/1996 | Shlyankevich |
| 2012/0121654 A1 | 5/2012 | Elder, Jr. et al. |
| 2012/0164190 A1 | 6/2012 | Elder et al. |
| 2013/0137916 A1 | 5/2013 | Goer |

FOREIGN PATENT DOCUMENTS

| EP | 2786751 A1 | 10/2014 |
| WO | 0115718 A1 | 3/2001 |
| WO | 01/95901 A1 | 12/2001 |
| WO | 2004069232 A2 | 8/2004 |
| WO | 2006/091187 A1 | 8/2006 |
| WO | 2007/000193 A1 | 1/2007 |
| WO | 2012/068140 A1 | 5/2012 |

OTHER PUBLICATIONS

Hillman et a l., 'Differential Effect of Soy Isoflavones in Enhancing High Intensity Radiotherapy and Protecting Lung Tissue in a Pre-Clinical Model of Lung Carcinoma'. Radiotherapy and Oncology. 109(1). pp. 1-16. Oct. 2013.
Baumann et al. Lung Cancer, "Dose and Fractionation Concepts in the Primary Radiotherapy of Non-Small Cell Lung Cancer", 2001 (S1) S35-S45.
Para et al. Radiotherapy and Oncology, "Effects of Genistein Following Fractionated Lung Irradiation in Mice", 2009 (92) 500-510.
Ekachai, Chukeatirote et al., "Antimicrobial property and antioxidant composition of crude extracts of Pueraria mirifica, Butea superha and Mucuna macrocarpa", Maejo International, Jurnal of Science and TecHnology, 2009, pp. 212-221, School of Science, Mae Fah Luang University, Chiang Rai 57100, Thailand.
Huang, Yufeng et al., "Long-Term Effects of Phytoestrogen Daidzein on Penile Cavernosal Structures in Adult Rats", Basic and Translational Science, 2007, Department of Reproduction and Genetics, Nanjing University School of Clinical Medicine, pp. 220-224.
Incrocci, L, "Erectile dysfunction and radiation therapy for prostate cancer". Department of radiation oncology, 2006, Elsevier SAS, pp. 116-120 .
Pan, Lianju et al., "Exposure to the Phytoestrogen Daidzein Attenuates Apomorphine-Induced Penile Erection Concomitant with Plasma Testosterone Level Reduction in Dose and Time-Related Manner in Adult Rats", Department of Reproduction and Genetics, Nanjing University School of Clinical Medicine, Basic Science, 2007, Department of Reproduction and Genetics, Nanjing University School of Clinical Medicine, pp. 613-617.
Ahmad, Iftekkhar U. et al, "Soy Isoflavones in Conjunction With Radiation Therapy in Patients With Prostate Cancer", Nutrition and Cancer, 2010, pp. 996-1000, Taylor and Francis Group, LLC.
Kimura, Masaki et al., "Radiation-Induced Erectile Dysfunction Using Prostate-Confined Modern Radiotherapy in a Rat Model", International Society for Sexual Medicine, 2011, pp. 2215-2226, J Sex Med.
Kimura, Masaki et al., "Role of Oxidative Stress in a Rat Model of Radiation-Induced Erectile Dysfunction", International Society for Sexual Medicine, 2012, pp. 1535-1549, J Sex Med.
Brenner et al, "Computer Tomography—An Increasing Source of Radiation Exposure", The New England Journal of Medicine, 2007, pp. 2277-2284.
Brenner et al, "Impact of Reduced Patient Life Expectancy on Potential Cancer Risk from Radiologic Imaging" Radiology, vol. 261, No. 1, Oct. 2011, pp. 1-2.

(Continued)

*Primary Examiner* — T. Victor Oh
(74) *Attorney, Agent, or Firm* — Sherrill Law Offices, PLLC

(57) ABSTRACT

A method for mitigating erectile dysfunction as an adverse side effect of radiation therapy for prostate cancer, comprising administration of a therapeutic dosage of genistein to a patient diagnosed with prostate cancer throughout only a primary administration period that commences a defined period of up to two weeks prior to commencement of radiation therapy for prostate cancer and extends beyond conclusion of the radiation therapy.

21 Claims, No Drawings

(56) References Cited

OTHER PUBLICATIONS

Brink et al., "Science to Practice: Can Antioxidant Supplements Protect Against the Possible Harmful Effects of Ionizing Radiation from Medical Imaging?", Radiology, vol. 264, No. 1, Jul. 2012, pp. 193-198.

Busey et al., "Patient Knowledge and Understanding of Radiation From Diagnostic Imaging", Jama Intern Med, vol. 173, No. 3, Feb. 11, 2013, pp. 239-241.

Hall, et al, "Cancer Risk From Diagnostic Radiology: The Impact of New Epidemiology Data", The British Journal of Radiology, vol. 85, 2012, pp. e1316-e1317.

Hricak, Hedving et al., "Managing Radiation Use in Medical Imaging: A Multifaceted Challenge", Radiology, vol. 258, No. 3, Mar. 2011, pp. 889-905.

Huppmann et al, "Radiation Risks from Exposure to Chest Computed Tomography", Elsevier Inc., Seminars Ultrasounds CT and MRI, 2010, pp. 14-28.

Kuefner, et al. "Effects of Antioxidants on X-Ray-Induced y-H2AX Foci in Human Blood Lymphocytes: Preliminary Observations", Radiology, vol. 264, No. 1, Jul. 2012, pp. 59-67.

Metzner et al, "Study on the Pharmacokinetics of Synthetic Genestein After Multiple Oral Intake in Post-menopausal women", Arzneimittelforschung, 2009, NCBI p. 1.

Miglorietti et al, "The Use of Computed Tomography in Pediatrics and the Associated Radiation Exposure and Estimated Cancer Risk", Jama Pediatrics. Jun. 10, 2013, pp. E1-E8.

Pearce et al., "Radiation Exposure from CT Scans in Childhood and Subsequent Risk of Leukaemia and Brain Tumors: A Retrospective Cohort Study", Institute of Health and Society et al., Jun. 7, 2012, pp. 1-7.

Prasain et al., "Simultaneous Determination of 11 Phytoestrogens in Human Serum Using a 2 min Liquid Chromatography/tandem Mas Spectrometry Method", J Chromatography B Analyt Tecnol Biomed Life Sci., Apr. 15, 2012, pp. 13-14.

pmcinside.com, "Bio-Shield-Radiation", Premier Micronutirent Corporation.

Redon et al., "y-H2AX as a Biomarker of DNA Damage induced by Ionizing Radiation in Human Peripheral Blood Lymphocytes and Artificial Skin", NIH Public Access, 2009, pp. 1-14.

Teunissen et al., "Determination and Validation of a Quantitative Assay for the Analysis of Tamoxifen with its Four Main Metabolites and the Flavonoids Daidzein, Genestein and Glycitein in Human Serum Using Liquid Chromatography Coupled with Tandem Mass Spectrometry", J Chromatography B Analyt Tecnol Biomed Life Sci., Aug. 15, 2009, p. 24.

Wang et al. "Rapid and Simple One-Step Membrane Extraction for the Determination of 8-Hidroxy-2'Deoxyguanosine in Human Plasma by a Combination of On-Line Solid Phase Extraction and LC-MS/MS", Journal of Chromatography B, 2011, pp. 3538-3543.

Wyns et al. "Development of a High-Throughput LC/APCI-MS Method for the Determination of Thirteen Phytoestrogens Including Gut Microbial Metabolites in Human Urine and Serum", J Chromatography B Analyt Tecnol Biomed Life Sci., Apr. 15, 2010, p. 13-14.

Singh Vijay K. et al., "Effects of Genistein Administration on Cytokine Induction in Whole-Body Gamma Irradiated Mice", International Immunopharmacology, Elsevier, Amsterdam, NL, vol. 9, No. 12, Nov. 1, 2009 (Nov. 1, 2009), pp. 1401-1410.

Hillman, Gilda, "Soy Isoflavones Radiosensitize Lung Cancer While Mitigating Normal Tissue Injury", NIH Public Access, Radiother Oncol, Nov. 2011, 101, pp. 329-336, Elsevier Ireland Ltd.

Hillman, Gilda, "Differential effect of Soy Isoflavones in Enhancing high intensity radiotherapy and protecting lung tissue in a preclinical model of lung carcinoma", www.thegreenjournal.com, Radiotherapy and Oncology, Elsevier Ireland Ltd, 2013.

Landauer M R et al., "Genistein Treatment Products Mice From Ionizing Radiation Injury", Journal of Applied Toxicology, Jan. 1, 2003, p. 379-385, vol. 23, No. 6, Wiley InterScience, Great Britain.

Shimoi, Kayoko et al.; "Radioactive Effect of Antioxidative in y-ray Irradiated Mice", Laboratory of Food Hygiene and Laboratory of Food Chemistry, School of Food and Nuticional Scince, University of Shizuoka; 1994, Carcingenesis vol. 15, No. 11 pp. 2669-2672.

Hosseinimehr, Sayed Jalal; "Trends in the Development of Radioprotective Agents", Foundation Review; Oct. 2007, Drug Discovery Today, vol. 12 Nos. 19/20, pp. 794-805.

Anonymous: "Long-Term Side Effects of Cancer Treatment", Internet, Mar. 2014 (Mar. 2014), Retrieved from the Internet: URL:http://www.cancer.net [retrieved on Aug. 3, 2014], p. 1-3.

Anonymous: "Radiation Biology, Safety and Protection for Today's Dental Team", Internet Retrieved from the Internet: URL:http://www.dentalcare.com, Apr. 2015, p. 1.

Section 2: "Biological Effects of Ionizing Radiation" In: "Principles of Radiation Protection", Jan. 2006 (Jan. 2006 ), HEW Publication (FDA) pp. 1-26.

ADMINISTRATION OF A THERAPEUTIC AMOUNT OF GENISTEIN TO MITIGATE ERECTILE DYSFUNCTION RESULTING FROM RADIATION THERAPY FOR PROSTATE CANCER ONLY THROUGHOUT A DEFINED ADMINISTRATION PERIOD COMMENCING SHORTLY BEFORE AND CONCLUDING AFTER RADIATION THERAPY

FIELD OF INVENTION

The invention relates to methods of mitigating erectile dysfunction as an adverse side effect of radiation therapy for prostate cancer.

BACKGROUND

The most common type of cancer in the United States is prostate cancer. The United States National Cancer Institute estimates that more than 238,000 new cases will occur in the United States in 2013. Although the incidence is high, so is the survival rate. Treatment options for localized prostate cancer include radiation therapy, radical prostatectomy, hormone therapy, and combinations thereof. External beam radiation is one of the more commonly used treatment options. One of the adverse side effects of radiation treatment for prostate cancer is erectile dysfunction, resulting from radiative collateral damage to the penis and penile bulb. The resultant erectile dysfunction may and often does have a significant impact on a patient's quality of life. Accordingly, a substantial need exists for a treatment regimen capable of reducing the severity and/or incidence of erectile dysfunction following radiation therapy for prostate cancer.

One study, self-acknowledged as suffering from a number of weaknesses that limit the value of the resultant data, including an insufficient number of subjects, an insufficient number of adverse events, an insufficient percentage of participants completing the program, and reliance upon participant self-evaluation and self-reporting, found that administration of 200 mg/day of soy isoflavone, containing a ratio of 1.1:1:0.2 genistein:daidzein:glycitein, during and after radiation therapy for prostate cancer, had the potential to ameliorate radiation toxicity, including the adverse side effect of erectile dysfunction. Ahmad, I., Forman, J., Sarkar, F., Hillman, G., Heath, E., Vaishampayan, U., Cher, M., Andic, F., Rossi, P., and Kucuk, O., (2010) *Soy Isoflavones in Conjunction With Radiation Therapy in Patients With Prostate Cancer Nutrition and Cancer*, 62(7), 996-1000. Other clinical trials found no beneficial effects of genistein or soy isoflavones.

The treatment regimen disclosed in the Ahmad et al. article inadequately mitigates the adverse side effect of erectile dysfunction following radiation therapy for prostate cancer.

Hence, a substantial need continues to exist for a method of mitigating the sexual adverse effect of erectile dysfunction associated with radiation therapy for prostate cancer.

SUMMARY OF THE INVENTION

The invention is directed to a method for mitigating erectile dysfunction as an adverse side effect of radiation therapy for prostate cancer, comprising administration of a therapeutic dosage of genistein to a patient diagnosed with prostate cancer throughout only a primary administration period that commences a defined period of up to two weeks prior to commencement of radiation therapy for prostate cancer and extends beyond conclusion of the radiation therapy.

DETAILED DESCRIPTION OF A PREFERRED EMBODIMENT

Theory

Chronic oxidative stress is a major indirect cause of radiation-induced injury to cellular macromolecules, leading to DNA damage, cell death, and persistent activation/inactivation of signaling molecules involved in vascular function and inflammation, thus resulting in aberrant wound healing. Oxidative stress in penile tissue plays a crucial role in the development of radiation therapy induced erectile dysfunction via activation of NADPH oxidase, which leads to development of chronic oxidative stress followed by persistent inflammation. NADPH-oxidase-derived reactive oxygen species are a major source of oxidative stress after radiation. Vascular NADPH oxidases produce superoxide anions or hydrogen peroxide molecules that impede the ability of endothelial-derived nitric oxide (NO) to cause vasodilation, both through reducing the bioavailability of NO and inhibiting components of its signaling pathway. This results in vasoconstriction, reduced blood flow to the tissue, and subsequent erectile dysfunction. Without intending to be limited thereby, it is believed that genistein's ability to mitigate the sexual adverse effect of erectile dysfunction associated with radiation therapy for prostate cancer is mediated via genistein's anti-inflammatory properties and its ability, when administered in therapeutically sufficient dosage, to scavenge the reactive oxygen species responsible for the cellular damage that results in erectile dysfunction.

Description

Administration of a therapeutically effective dosage of genistein to a patient diagnosed with prostate cancer during only a primary administration period that commences a defined period of up to two weeks prior to commencement of radiation therapy for prostate cancer and extends beyond conclusion of the radiation therapy, can mitigate the adverse side effect of erectile dysfunction associated with such radiation therapy.

Commencing administration of genistein more than two weeks prior to commencement of radiation therapy for prostate cancer increases the cost of the therapy in the absence of a concomitant enhancement in mitigation of radiation therapy induced erectile dysfunction and unnecessarily delays commencement of radiation therapy, in the absence of a concomitant enhancement in mitigation of radiation therapy induced erectile dysfunction.

The Active Agent

Genistein belongs to the pharmacological classes of soy isoflavone, flavonoid, polyphenol and phytoestrogen. It is also known as 5,7-dihydroxy-3-(4-hydroxyphenyl)-chromen-4-one (IUPAC), 5,7-dihydroxy-3-(4-hydroxyphenyl)-4H-1-benzopyran-4-one, 5,7,4'-trihydroxyisoflavone, 4',5,7-trihydroxyisoflavone, Genestein, Prunetol, Sophoricol and Differenol A. It has a Molecular Formula of $C_{15}H_{10}O_5$, a Molecular Weight of 270.237 g/mol (270.24 daltons), a Chemical Abstracts Service (CAS) Registry Number 446-72-0 and a Beilstein Registry Number 263823. It is commercially available from a number of sources, including DSM Nutritional Products, Inc. of Basel, Switzerland under Drug Master File (DMF) #19747-PIND #104,709.

Administration

Administration Route

Genistein can be administered by virtually any of the commonly accepted practices for the administration of pharmaceutical preparations including specifically, but not exclusively, mucosal administration, oral consumption, ocular administration, subcutaneous injection, transdermal administration, intravascular administration, intramuscular administration, etc. Oral administration is generally preferred.

Mucosal administration of genistein includes such routes as buccal, endotracheal, nasal, pharyngeal, rectal, sublingual, vaginal, etc. For administration through the buccal/sublingual/pharyngeal/endotracheal mucosal, genistein may be formulated as an emulsion, gum, lozenge, spray, tablet or an inclusion complex such as cyclodextrin inclusion complexes. Nasal administration is conveniently conducted through the use of a sniffing powder or nasal spray. For rectal and vaginal administration, genistein may be formulated as a cream, douche, enema or suppository.

Oral consumption of genistein may be effected by incorporating the genistein into a food or drink, or formulating the genistein into a chewable or swallowable tablet or capsule. The genistein is preferably orally administered as a nano-suspension in accordance with U.S. Patent Application Publications 2012/0164190 and 2012/0121654, both hereby incorporated by reference.

Genistein is virtually insoluble in water, thereby limiting its bioavailability when administered orally. Genistein provided as a nano suspension in accordance with US Patent Application Publications 2012/0164190 and 2012/0121654 has significantly improved oral bioavailability. This allows dosing without medical supervision, which enables pre-dosing at home prior to known and planned instances of radiation therapy. To further improve oral bioavailability, genistein can also be incorporated as sub-micron size particles in an orally ingestible formulation. Generally, a dose of ~1 g per day of genistein provided as a nanosuspension should be effective for achieving the desired mitigating protective effect.

Ocular administration may be effected by incorporating genistein into a solution or suspension adapted for ocular application such as drops or sprays.

Subcutaneous, intravascular and intramuscular administration involves incorporating the genistein into a pharmaceutically acceptable and injectable carrier.

For transdermal administration, the genistein may be conveniently incorporated into a lipophilic carrier and formulated as a topical cream or adhesive patch.

Administration Dosage and Timing

The range of dosages effective for achieving the desired mitigation of erectile dysfunction associated with radiation therapy of prostate cancer may be determined in accordance with standard industry practices. The desired protective effect can generally be achieved by administration of at least ~1 gram of genistein per day, preferably at least ~1.2 grams of genistein per day and most preferably at least ~1.5 grams of genistein per day, taken as a single dose or multiple doses each day. Lower amounts may also be therapeutic.

Genistein administered for a short-term prior to commencement of radiation therapy for prostate cancer, throughout such therapy and after conclusion of such therapy is effective for mitigating erectile dysfunction associated with radiation therapy for prostate cancer. Administration of a therapeutic amount of genistein more than two weeks prior to commencement of radiation therapy for prostate cancer contributes little towards mitigation of this adverse side effect and is therefore discouraged as unnecessary.

Administration Period

The administration of genistein commences prior to commencement of radiation therapy for prostate cancer, but no more than two weeks prior, with a preference for commencement no more than one week prior, most preferably no more than three days prior. Administration continues throughout the radiation therapy and continues after conclusion of the radiation therapy.

The primary administration of genistein should continue for at least one month after conclusion of the radiation therapy, with a preference for continued administration for at least two months, most preferably at least six months. A primary administration period that continues for a period of less than one month after conclusion of the radiation therapy tends to result in a precipitous decline in the percentage of treated patients benefiting from the protective effect of such administration, while an extended period of administration can continue to benefit the patient.

A reduced maintenance amount of genistein may be administered for a period after completion of the primary administration of genistein. The reduction may be in the form of a reduced dosage (e.g., reduced to less than 60% the amount administered during the therapeutic stage) and/or a reduced frequency (e.g., ½ or ¼ the frequency during the therapeutic stage). When employed, the maintenance period should last for at least one month, preferably at least three months and most perferably at least six months. Shorter durations tend to diminish the benefit obtained by administration of a maintenance dosage, while administration of some maintenance amount of genistein can perpetually benefit the patient.

We claim:

1. A method for mitigation of erectile dysfunction as an adverse side effect of radiation therapy for prostate cancer, comprising administration of a therapeutic dosage of genistein to a patient diagnosed with prostate cancer throughout only a primary administration period that commences a defined period of up to two weeks prior to commencement of radiation therapy for prostate cancer and extends beyond conclusion of the radiation therapy.

2. The method of claim 1 wherein the primary administration period commences at least one week prior to commencement of radiation therapy for prostate cancer.

3. The method of claim 1 wherein the primary administration period commences at least three days prior to commencement of radiation therapy for prostate cancer.

4. The method of claim 1 wherein the primary administration period continues for at least one month after completion of radiation therapy for prostate cancer.

5. The method of claim 1 wherein the primary administration period continues for at least two months after completion of radiation therapy for prostate cancer.

6. The method of claim 1 wherein the primary administration period continues for at least three months after completion of radiation therapy for prostate cancer.

7. The method of claim 1 wherein the primary administration period continues for at least six months after completion of radiation therapy for prostate cancer.

8. The method of claim 1 wherein a maintenance dosage of less than 60% of the amount of the therapeutic dosage is administered during a maintenance period after completion of the primary administration period.

9. The method of claim 8 wherein the maintenance period is at least one month.

10. The method of claim 8 wherein the maintenance period is at least three months.

11. The method of claim 8 wherein the maintenance period is at least six months.

12. The method of claim 1 wherein a maintenance dosage is administered during a maintenance period after completion of the primary administration period, and wherein the maintenance dosage is administered at a frequency that is one-half or less of the frequency at which the therapeutic dose was administered.

13. The method of claim 1 wherein a maintenance dosage is administered during a maintenance period after completion of the primary administration period, and wherein the maintenance dosage is administered at a frequency that is one-quarter or less of the frequency at which the therapeutic dose was administered.

14. The method of claim 12 wherein the maintenance period is at least one month.

15. The method of claim 13 wherein the maintenance period is at least three months.

16. The method of claim 12 wherein the maintenance period is at least six months.

17. The method of claim 1 wherein the genistein is administered in the form of a nanosuspension.

18. The method of claim 1 comprising administration of at least 1 gram per day of genistein.

19. The method of claim 1 comprising administration of at least 1.2 grams per day of genistein.

20. The method of claim 1 comprising administration of at least 1.5 grams per day of genistein.

21. The method of claim 1 wherein administration is effected orally.

* * * * *

UNITED STATES PATENT AND TRADEMARK OFFICE
CERTIFICATE OF CORRECTION

PATENT NO. : 9,623,004 B2
APPLICATION NO. : 14/446906
DATED : April 18, 2017
INVENTOR(S) : Kaytor et al.

Page 1 of 1

It is certified that error appears in the above-identified patent and that said Letters Patent is hereby corrected as shown below:

In the Specification

At Column 1, Line 10, before the heading FIELD OF INVENTION, please add the following new paragraph:
-- GOVERNMENT SUPPORT
This invention was made with government support under STTR Grant Number R41CA186431 awarded by the US Department of Health and Human Services, National Cancer Institute. The government has certain rights in this invention. --

Signed and Sealed this
Second Day of January, 2024

Katherine Kelly Vidal
*Director of the United States Patent and Trademark Office*